United States Patent [19]

Nelson

[11] 4,118,404

[45] Oct. 3, 1978

[54] PROCESS FOR PREPARING ALKANOL AMIDE COMPOSITIONS

[75] Inventor: Gunner E. Nelson, Baton Rouge, La.

[73] Assignee: Ethyl Corporation, Richmond, Va.

[21] Appl. No.: 397,672

[22] Filed: Sep. 17, 1973

[51] Int. Cl.$^2$ .......... C07C 103/38

[52] U.S. Cl. .......... 260/404; 252/548

[58] Field of Search .......... 260/404

[56] References Cited

U.S. PATENT DOCUMENTS

| | | | |
|---|---|---|---|
| 3,232,697 | 2/1966 | Needleman | 260/404 X |
| 3,257,436 | 6/1966 | Lindner | 260/404 |
| 3,385,755 | 5/1968 | Seebohm et al. | 260/404 X |
| 3,503,891 | 3/1970 | Schimbor | 252/548 |
| 3,651,104 | 3/1972 | Siddall | 260/404 X |

*Primary Examiner*—Patrick P. Garvin

*Attorney, Agent, or Firm*—Donald L. Johnson; John F. Sieberth; Paul H. Leonard

[57] ABSTRACT

A process for producing novel alkanol amide compositions of low melting point is disclosed. It involves reacting alkanol amines with esters whose acyl groups include some groups with a positioned alkyl group side chains containing two or more carbon atoms. The novel alkanol amide compositions produced in the process exhibit useful and valuable properties particularly when used in combination with various detergents in aqueous washing solutions as set forth herein.

29 Claims, No Drawings

PROCESS FOR PREPARING ALKANOL AMIDE COMPOSITIONS

BACKGROUND OF THE INVENTION

This invention relates to the preparation of alkanol amides of fatty acids whose acyl groups have from about 8 to about 20 carbon atoms, to mixtures of such amides, and to uses of such mixtures.

The production of alkanol amides by a reaction with alkanol amines of esters derived from natural oils and fats in a base catalyzed process has been known for some time. The process is described in U.S. Pat. Nos. 2,464,094; 2,877,246; 3,107,258; 3,257,436 and 3,395,162 and in J. Am. Chem. Soc. 64, 2498 (1942). The process produces monoalkanol amides when using monoalkanol amines as reactant while it produces dialkanol amides when using dialkanol amines as reactant.

The monoalkanol amides are useful in detergent compositions as described in U.S. Pat. Nos. 2,383,737 and 3,332,878. The dialkanol amides also are useful in detergent compositions as described in U.S. Pat. Nos. 2,607,740 and 2,870,091.

In many instances the dialkanol amides are preferred because of convenient, low, melting points which permit handling as liquids at ordinary temperatures of 25°–75° C. Unfortunately, this virtually has required the use of natural source ester materials because there has been no convenient source of usable synthetic esters for the base catalyzed reaction with dialkanol amines as that process is known from the prior art. One of the preferred sources of low cost synthetic source esters is via the catalytic reaction of olefins with CO and alcohol as described for example in U.S. Pat. Nos. 3,168,553. Unfortunately, the esters obtained this way do not react readily with dialkanol amines. An aspect of this invention is the discovery that this trouble is caused by the presence in such synthetic esters of a substantial percentage (15–50 percent) of esters having branched chain acyl groups, many of which acyl groups have α-ethyl, α-propyl, α-butyl and higher alkyl group substitution located in the carbon chain position alpha (α) to the carbon atom of the $$(-\underset{O}{\underset{\|}{C}}-)$$

group.

To avoid this problem of poor reactivity of branched esters it has been necessary in the past to use the prior art acyl halide route wherein an acid having a desired acyl group such as dodecanoic or tridecanoic is converted to acyl halide, such as acyl chloride, and then the acyl halide is reacted with dialkanol amine. U.S. Pat. Nos. 2,411,434 and 3,503,891 describe such processing.

SUMMARY OF THE INVENTION

In accordance with the invention, a new process is provided which produces novel alkanolamide compositions useful in various ways such as foam boosters for washing compositions, as fabric treating agents, and the like.

A feature of the invention is the discovery that lower alkyl esters of aliphatic monocarboxylic acids whose acyl groups contain from about 8 to about 20 carbon atoms and are branched carrying in the α position (of the acyl groups) an alkyl substituent at least two carbon atoms in length are substantially unreactive with di lower alkanol amine but do react with mono lower alkanol amine and that by applying a two step reaction sequence, alkanol amines having high purity and new, highly desirable, properties can be obtained readily and at low cost from ester mixtures containing these esters.

The significance of this discovery is that it permits the production of valuable dialkanol amides having low melting points, by the ester-amine amidation reaction, using esters produced synthetically and which contain some branched chain acyl groups. The invention thus satisfies a long felt need of providing new amides at low cost from synthetically produced acyl groups. Not only are the new synthetic amides at least equivalent to the prior art amides in most performance aspects, but they are actually superior to the prior art amides in selectable properties.

Accordingly, the present invention relates to a process for producing alkanol mixtures in which a di lower alkanol amine is reacted with a mixture of lower alkyl esters of aliphatic monocarboxylic acids whose acyl groups contain from about 8 to about 20 carbon atoms. The mixture of esters reacted is characterized in that from about 2 to about 20 mol percent of said ester mixture is branched ester in which the acyl groups carry in the α position an alkyl substituent at least two carbon atoms in length. The esters which are of this branched structure are substantially unreactive with the dialkanol amine and therefore are not converted to amide although other esters co-present may react with the dialkanol amine to produce dialkanol amides. The amount of dialkanol amine employed in this reaction is sufficient to convert at least 10 mol percent of the ester mixture into dialkanol amide. The product from the preceding reaction which contains dialkanol amide plus unreacted ester is subsequently reacted with mono lower alkanol amine to convert unreacted ester into mono lower alkanol amide thus producing a mixture of dialkanol amide and monoalkanol amide. In this second reaction, the esters that did not react in the first reaction, including the branched ester, react readily to produce virtually complete overall conversion of feed esters to amide without a need for large excess of either unreacted amine or unreacted ester to remain in the amide product unless such is desired and brought about by the use of excess of one reactant or the use of conditions which bring about only partial reaction. Preferably both said reactions are carried out in the presence of a base catalyst.

It has been discovered that alkanol amides produced by the foregoing process have excellent properties in detergent compositions. The amides are a mixture of mono lower alkanol amides and di lower alkanol amides in which the acyl groups contain from about 8 to about 20 carbon atoms. At least 10 mol percent of the mixture is di lower alkanol amide. From about 2 to about 20 mol percent of the amide mixture is mono lower alkanol amide whose acyl groups carry in the α position an alkyl substituent at least two carbon atoms in length.

According to another aspect of the invention, a washing composition is provided consisting essentially of (1) a mixture of mono and di lower alkanol amides in which the acyl groups are open chain acyl groups containing from about 8 to about 20 carbon atoms, said mixture being characterized in that at least 10 mol percent thereof is di lower alkanol amide and further in that from about 2 to about 20 mol percent of said mixture is mono lower alkanol amide whose acyl groups carry in the $\alpha$ position an alkyl substituent at least two carbon atoms in length; and (2) an organic detergent surfactant selected from the group consisting of anionic detergents, cationic detergents, nonionic detergents, ampholytic detergents, zwitterionic detergents, and mixtures thereof suitable for use in water. The amount of amide in the washing composition ranges from about 0.05 to about 25 percent by weight. This washing composition is preferably used to form with water an aqueous washing system. The amount of amide used in such a system ranges from about 0.05 to about 25 percent by weight of the total of amide and organic detergent surfactant. The total of amide and organic detergent surfactant in such a system is from about 0.05 to about 1.0 weight percent of the system.

In addition to the foregoing, the present invention relates to an improvement in a method for washing articles in an aqueous solution of alkanol amide composition and organic detergent surfactant using the foregoing washing composition.

DESCRIPTION OF THE INVENTION

Alkanol amides, also called hydroxy alkyl amides, have valuable detergent properties. They are used with various detergents to enhance foaming, particularly in aqueous solutions, to enhance (increase) the viscosity of washing solutions, to form synergistic cleaning mixtures, and in other ways well known to those skilled in the art. In many instances, alkanol amides having low melting points are particularly desired to facilitate the handling thereof as liquids at moderate temperatures such as 25°-75° C.

By virtue of the present invention, a new amidation process is provided which can utilize the base catalyzed reaction of alkanol amines with esters having a significant percentage of branched chain acyl groups. The present process for producing alkanol amides preferably utilizes a mixture of esters containing some esters whose acyl groups (acid radicals) are of branched chain carbon skeletal structure having $\alpha$ positioned alkyl groups or branches containing two or more carbon atoms each such as $\alpha$-ethyl, $\alpha$-propyl, and $\alpha$-butyl, and higher alkyl. In the first stage of the present process, the esters are reacted with di lower alkanol amine. Lower alkyl esters of aliphatic monocarboxylic acids whose acyl groups have from about 8 to about 20 carbon atoms and wherein the $\alpha$ carbon atom of the acyl groups is free of $\alpha$ positioned alkyl branches having more than one carbon atom react readily with di lower alkanol amines to produce di lower alkanol amides leaving virtually unreacted co-present esters whose acyl groups carry ethyl, propyl, butyl, or higher alkyl branches on the $\alpha$ carbon atom of the longest carbon chain. Preferably the amount of di lower alkanol amine fed at the first stage of the process is not in excess of that required to react with the portion of the feed esters whose acyl groups are free of $\alpha$ positioned alkyl branches having two or more carbon atoms. Thus the presence of excess dialkanol amine in the produce amide is avoided or minimized.

The first stage, or intermediate, product is a mixture containing (1) di lower alkanol amides whose acyl groups are free of $\alpha$ positioned alkyl branches having more than one carbon atom plus (2) unreacted ester including ester whose acyl groups carry an ethyl, butyl or higher order alkyl branch at the $\alpha$ carbon atom. The intermediate product is then reacted with mono lower alkanol amine in a second stage. The unreacted ester in the intermediate product reacts readily in the second stage to produce mono lower alkanol amide. Preferably the amount of mono lower alkanol amine fed at the second stage is not in excess of that required to react with the unreacted ester in the intermediate product.

The present process may be performed in a batch, semi-continuous or continuous manner. The order of addition of the reactants in each step is not particularly critical; however, the sequence of reaction of ester with di lower alkanol amine and then with mono lower alkanol amine is important. For ease of control, it is preferred that in the first stage the di lower alkanol amine is added intermittently or continuously to the ester-containing reaction mixture and that in the second stage the mono lower alkanol amine is added intermittently or continuously to the amide-containing reaction mixture from the first stage.

To simplify overall operations and reduce handling and other processing expenses, the present two-step processing sequence is preferably applied in a single operating sequence to starting ester mixtures which have the desired distribution in regard to molecular weight (or number of carbon atoms per acyl group) and in regard to various lengths of $\alpha$ positioned alkyl branches thereby producing directly the desired amide product without requiring subsequent analyses and blending of amides. Ester mixtures used in the present process may be obtained by blending various suitable synthetic or natural source esters in appropriate proportions.

Following the amidation reactions it is usually desirable first to allow the product to stand for a period of time of from about 1 minute to about 48 hours at a temperature of from about 25° to about 150° C. to permit redistribution (stabilization) to take place.

Following the redistribution, where such is used or subsequent to the second stage where there is no redistribution step, it is usually desirable to inactivate the catalyst remaining in the second stage reaction product by neutralization thereof with a suitable organic or inorganic acid. Suitable acids include $H_2SO_4$, HCl, acetic acid, and the like. Normally the neutralization products are allowed to remain in the product amide since the amounts thereof is quite small on a weight basis.

In particularly preferred esters used in the present process, from about 5 to about 10 mol percent of said mixture is branched ester in which the acyl groups carry in the $\alpha$ position an alkyl substituent at least two carbon atoms in length.

Numerical values for the mol ratio of dialkanol amine to lower alkyl esters employed in the first reaction of the present process vary somewhat depending upon the starting esters and the product amide desired but in general they range from about 0.25:1 to about 1.5:1. A preferred upper limit on the mol ratio of dialkanol amine to ester fed is about 1.2:1. Where particularly outstanding product amides are desired for detergent compositions, the ratio of dialkanol amine to ester fed at the first reaction is preferably in the range of about 0.4:1 to about 1:1. For more highly preferred detergent compositions using the preferred ester feed obtained by the reaction of olefins with CO and methanol, the ratio of dialkanol amine to ester is from about 0.5:1 to about 0.9:1.

In a specific embodiment, the amount of dialkanol amine fed at the first stage is that which produces a product amide mixture which is about 50 mol percent dialkanol amide. Product amides have excellent viscosity and washing properties.

In another specific embodiment, the amount of dialkanol amine fed at the first stage is that which produces a product amide mixture which is about 70 mol percent dialkanol amide. Product amides have excellent viscosity and washing properties and in addition have convenient melting points for many uses.

In another specific embodiment, the amount of dialkanol amine fed at the first stage is that which produces a product amide mixture which is about 90 mol percent dialkanol amide. Product amide is outstanding in terms of melting points and viscosity properties.

Where maximum dialkanol amide content and low melting point are desired, the amount of dialkanol amine supplied at the first stage of the process is about 100 percent of the stoichiometric amount required for reaction of all of the feed esters whose acyl groups carry no α positioned branch with two or more carbon atoms. Preferably this is the maximum amount of dialkanol amine used where high purity of product is desired.

The amount of mono lower alkanol amine fed at the second stage is preferably not substantially in excess of the amount required to react with all unreacted ester remaining at that point in the intermediate product from the first stage. Although one may feed even large amounts of excess amine as far as the process itself is concerned, usually it is preferred to minimize purification and recovery problems of product amides and thereby simplify the overall process by holding the amount of excess mono lower alkanol amine fed below 20 percent, preferably below about 5 percent. The mol ratio of monoalkanol amine to unreacted ester in the second reaction preferably is in the order of from about 0.9:1 to about 1.2:1, especially about 1:1. This holds to a low value the amount of excess amine in the product on the one hand and on the other hand holds to a low value the amount of excess ester in the product.

To provide preferred ratios in the overall process, including a high content of dialkanol amide suitable for most feed esters containing 10 percent or less of said branched ester, the mol ratio of dialkanol amine to lower alkyl esters employed in the first reaction falls in the range of about 0.5:1 to about 0.9:1 and the mol ratio of monoalkanol amine to said unreacted ester in the second reaction is in the order of about 1:1.

In elaboration of the foregoing, it is evident that acyl groups which are free of α positioned alkyl branches having more than one carbon atom include acyl groups whose α carbon atoms carry two hydrogen atoms, those whose α carbon atoms carry two methyl groups and those whose α carbon atoms carry a hydrogen atom and a methyl group. The length of the α positioned alkyl branches which contain two or more carbon atoms each ranges upward from ethyl to include alkyl groups with a whole number of carbon atoms which does not exceed (n-2/2) wherein *n* is the total numbers of carbon atoms in the acyl group. Preferably the esters or amides with α positioned alkyl branches which contain two carbon atoms are most numerous, there being progressively smaller amounts of esters or amides containing the longer branches. Thus the esters with ethyl branches outnumber the esters with propyl branches which in turn outnumber the esters with butyl branches, and so forth.

Preferred esters used in the present invention usually contain not only branched esters whose acyl groups carry in the α position an alkyl substituent at least two carbon atoms in length but also contain some α branched esters wherein the only α substituency is methyl. Such α-methyl branched esters react readily with the dialkanol amine of the present process and when in admixture with α-ethyl, α-propyl, etc. branched esters react preferentially relative thereto with the dialkanol amine in the first reaction of the process leaving substantially all of the α-ethyl, α-propyl, etc. branched esters unreacted and in the intermediate product fed to the second stage to react with monoalkanol amine in the second reaction.

Generally speaking, ester for the first reaction is preferred wherein from about 10 to about 65 mol percent of the ester mixture used in the first reaction is branched ester in which the acyl groups carry a methyl group in the α position. Such ester mixtures are desired for their low cost, for their excellent reactivity in the present process and for the valuable properties of the products produced therefrom when using the present process. Especially preferred ester mixtures in regard to this aspect are those wherein from about 12 to about 25 mol percent of the mixture is branched ester in which the acyl groups carry a methyl group in the α position.

The α carbon atoms of the acyl groups of particularly preferred esters carry at least one hydrogen atom. Preferred esters used in the present invention usually contain not only the foregoing branched esters which carry methyl, ethyl, propyl, etc. alkyl groups on the α carbon atoms of the acyl groups but in addition contain some esters which carry two hydrogen atoms on the α carbon atoms of the acyl groups.

The preferred esters which carry on the α carbon atoms of their acyl groups two hydrogen atoms or which carry on the α carbon atoms of their acyl groups one hydrogen atom and one methyl group react readily with di lower alkanol amine at the first stage reaction and produce excellent dialkanol amides provided the esters remaining can be converted to monoalkanol amides as in the present process. Without such subsequent conversion, however, the amides at this point usually are too impure to compete successfully with natural source dialkanol amides. In addition, if an inadequate amount of di lower alkanol amine is available at the first stage so that some of these hydrogen-hydrogen or hydrogen-methyl esters cannot react at the first stage, these esters react readily with the mono lower alkanol amine in the second stage reaction. Thus, at the second stage reaction, preferred esters of the intermediate product fed thereto can include (1) esters whose acyl groups carry two hydrogen atoms at the α carbon atoms, (2) esters whose acyl groups carry at the α carbon atom one hydrogen atom and one methyl group, and (3) esters whose acyl groups carry at the α carbon atom one hydrogen atom and one alkyl group having two or more carbon atoms.

The product obtained from such ester mixtures in the present two-stage processing when using in the first stage less than a stoichiometric amount of di lower alkanol amine for all the esters therefore may contain the first three components of the following list and may contain the fourth and even some fifth components depending upon proportions:

1. Dialkanol amides carrying two hydrogen atoms on the α carbon atom of the acyl groups
2. Dialkanol amides carrying a methyl branch on the α carbon atom of the acyl groups 3. Monoalkanol amides carrying an ethyl, propyl, butyl or higher alkyl branch on the α carbon atom of the acyl groups
4. Monoalkanol amides carrying a methyl branch on the α carbon atom of the acyl groups
5. Monoalkanol amides having two hydrogen atoms on the α carbon atom of the acyl groups The esters used in the present process are lower alkyl esters of carboxylic acids as set forth hereinbefore and of lower alkanols. It is evident that such esters are generally referred to as alkyl esters corresponding to the hydrocarbon group of the alcohol component thereof; for example, methyl esters are based on methyl alcohol. It will be recognized that this term is distinct from the terms α-methyl, α-ethyl, 2-methyl, 2-ethyl, etc. used to characterize the length and location of branches in the acyl groups of the esters.

Preferred esters reacted are methyl esters. Such esters have excellent reactivity, are easily made, and in the amidation reaction liberate alcohol which is readily recycled. In addition to methyl esters, other alkyl esters of $C_8$–$C_{20}$ monocarboxylic acids can be used such as esters of ethyl, propyl, and butyl alcohol but for commercial and other reasons they are less preferred than the esters of methyl alcohol.

In general, the acyl segment of the esters used in the present process may be selected from a large group. The esters may be derived from straight chain and branched chain, saturated and unsaturated, aliphatic monocarboxylic acids including caprylic acid, capric acid, stearic acid, lauric acid, myristic acid, palmitic acid, oleic acid, linoleic acid, linolenic acid, undecanoic acid, 2-methyl decanoic acid, 2-ethyl nonanoic acid, tridecanoic acid, 2-methyl dodecanoic acid, 2-ethyl undecanoic acid, pentadecanoic acid, 2-methyl tetradecanoic acid, 2-ethyl tridecanoic acid, 3-ethyl undecanoic acid, 4-propyl decanoic acid, and the like. Suitable esters may be derived from mixed higher fatty acids or esters derived from animal or vegetable sources, for example, lard, coconut oil, rapeseed oil, sesame oil, palm kernel oil, palm oil, olive oil, corn oil, cottonseed oil, sardine oil, tallow, soya bean oil, peanut oil, castor oil, seal oils, whale oil, shark oil, and other fish oils; from partially or completely hydrogenated animal and vegetable oils such as those mentioned; from fatty and similar acids or esters derived from various waxes such as beeswax, spermaceti, montan wax, coccerin, and carnauba wax. In addition, suitable esters may be obtained from higher molecular weight carboxylic acids derived by oxidation or other chemical processing methods from various starting materials including paraffin wax, petroleum and similar hydrocarbons.

Particularly preferred esters for the present process are produced by a carbonylation reaction of olefinic hydrocarbons having from about 7 to about 19 carbon atoms per molecule, with CO and with a hydroxyl compound such as methyl alcohol using various catalysts such as nickel, cobalt, iridium, rhodium, palladium, sulfuric acid, or carbonyls such as cobalt carbonyl, etc. This process produces directly mixtures of esters having branched and unbranched carbon chain acyl groups. This process is described, for example, in U.S. Pat. No. 3,168,553. Alternately, branched acids or salts can be produced by other processes and later esterified with a lower alkanol such as methanol or ethanol. Branched acids can be produced in several ways such as shown by U.S. Pat. Nos. 2,607,787; 2,831,877; 2,876,241; 3,205,244; 3,296,286; 3,530,155; 3,661,951; 3,661,957; 3,678,083; and 3,718,676. Branched esters are also produced via esterification of acids obtained via oxidation of isoaldehydes, via ozonolysis of olefins, via caustic fusion of synthetic or natural source alcohols, and in other processing as described in U.S. Pat. Nos. 2,010,358; 2,042,220, 2,607,787 and 2,883,426. Thus directly or indirectly via other processing such as esterification and blending one obtains methyl, ethyl or other alkyl esters having from about 8 to about 20 carbon atoms per acyl group and containing from about 10 to about 50 percent branched chain acyl groups, a proportion of which of from about 2 to about 20 mol percent of the total acyl groups, has ethyl, propyl, butyl or higher alkyl branches carried by the α carbon atoms of the acyl groups.

Preferred esters used in the present process are esters of aliphatic monocarboxylic acids whose acyl groups have from about 11 to about 15 carbon atoms. Such esters are characterized by excellent reactivity in the process and by particularly useful properties of the product amides. Particularly preferred are ester mixtures wherein some acyl groups have 11 carbon atoms, some acyl groups have 13 carbon atoms and some acyl groups have 15 carbon atoms. In addition to excellent reactivity, such ester mixtures have the advantage that they are readily produced at low cost. Outstanding esters useful in the present process are esters in which the acyl groups have 13 carbon atoms. Although pure $C_{13}$ methyl ester mixtures are likely to be more expensive than the $C_{11}$, $C_{13}$ and $C_{15}$ mixtures aforesaid, the $C_{13}$ amide products obtained via the present process have outstanding properties in regard to viscosity in aqueous solutions. Ester mixtures rich in esters with $C_{13}$ acyl groups (from about 40 to about 50 mol percent) are especially desired for all around excellent reactivity, low cost and ready availability and for excellence of amide product.

Preferred olefins reacted with CO and methanol or CO and water to provide starting materials for the present process have from about 10 to about 14 carbon atoms per molecule, including decene-1, undecene-1, dodecene-1, tridecene-1, tetradecene-1, dodecane-2, 2-ethyl decene-1, 2-propyl nonene-1, 3-ethyl decene-1, and the like. Preferred olefins of the about 7 to about 19 carbon atoms per molecule range as well as of the about 10 to about 14 carbon atoms per molecule range have even numbers of carbon atoms per molecule; however, other olefins such as olefins having 7, 9, 11, 13, 15, 17 and 19 carbon atoms can be used to produce materials with acyl groups having even numbers of carbon atoms. Frequently it is convenient to select olefins for this process to provide directly, without need for separate production, analysis, or blending of esters or of amide, the desired distribution of carbon atoms in the acyl groups of the amide product as set forth herein. Preferred olefins reacted to produce esters or acids are predominantly terminal olefins and preferably of predominantly straight chain carbon skeleton (unbranched) and substantially free of remote branches carried at the β, δ, or γ carbon atoms or further removed from the

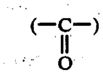

group. Branched skeleton olefins may be used and may give rise to branched esters whose acyl groups contain side chain alkyl groups. Although pure esters are preferred, the present process does not require the removal of all residual unreacted olefins in admixture with the starting esters since such olefins can be separated from the amides and recycled.

In general, the alkanol amines useful include symmetrical, unsymmetrical, normal and iso derivatives, such as monoethanol amine, diethanol amine, monoisopropanol amine, diisopropanol amine, monopropanol amine, dipropanol amine, monobutanol amine, dibutanol amine, monopentanol amine, dipentanol amine, monohexanol amine, dihexanol amine, monoethyl monoethanol amine, methoxypropan-ol-3; 2-N-methylaminopropandiol-1,3; monoethanol monopropanol amine, monoethanol monobutanol amine; alkylol polyamines such as alkylol derivatives of ethylene diamine, diethylene triamine, and triethylene tetra-amine as, for example, hydroxy ethyl ethylene diamine, diglycerol monoamine, diglycerol-di-amine, hydroxy-alkyl amines derived from other polyhydric alcohols, including glycols, sugars and sugar alcohols such as ethylene glycol, diethylene glycol, glycerol, dextrose, sucrose, sorbitol, mannitol and dulcitol.

The amines used in the reaction are preferably lower alkanol amines having from 2 to about 4 carbon atoms per alkanol group. These amines are preferred because of their excellent reactivity and because of the properties of product amides obtained when such amines are used. Particularly preferred amines used in the first and second reactions are diethanol amine and monoethanol amine, respectively. Other preferred amines are diisopropanol amine and monoisopropanol amine, respectively.

The physical conditions used in the reactions are not particularly critical and in general are similar to those known in the prior art for individual reactions of natural source esters with dialkanol amine or with monoalkanol amine. Conditions for the first reaction are similar to those used for the prior art reaction of diethanol amine with natural source esters such as methyl esters obtained from coconut oil by transesterification wherein the product is dialkanol amide. Conditions for the second reaction are similar to those used for the prior art reaction of monoethanol amine with the natural source esters.

Thus temperatures in the range of about 25° C. to about 150° C. are preferred for each of said reactions. Especially preferred temperatures are in the range of about 40° C. to about 75° C. for the first reaction and in the range of about 75° C. to about 125° C. for the second reaction. Since the second reaction is usually somewhat slower than the first reaction, it is usually preferred to employ a higher temperature in the second reaction than in the first reaction. Typical temperatures are about 60° C. and about 105° C. for the first and second stages, respectively. Pressures depend to some extent upon temperature and range from about 5 mm of mercury absolute to about 25 atmospheres with absolute pressures of from about 10 mm to about 760 mm preferred. Typical pressures are about 30 mm of mercury absolute, about 100 mm of mercury absolute and about atmospheric pressure.

Catalysts are frequently employed to advantage in the reactions particularly in the second stage reaction. Catalysts may be dispensed with in the first reaction particularly when the higher temperatures of 100°–150° C. are used; however, since it is usually desired to have a catalyst at the second reaction, it is preferred to add an effective amount of the catalyst at the first reaction and conduct the first reaction under the lower temperatures indicated for catalyzed reaction carrying the catalyst through to the second step reaction.

Any suitable catalyst may be used in the present process. Known catalysts include salts, such as the hydrochloride of the amine used, and base catalysts, such as an alkali metal, an alkali metal alkoxide, amide or other alkali metal compound which will generate an alkali metal alkoxide on contact with an alcohol. Preferred catalysts are alkali metals, alkali metal alkoxides, and alkali metal amides. Of these, the alkali metal alkoxides, especially those containing from 1 to 5 carbon atoms, are particularly preferred because of their excellent catalytic activity and ease of use and ease of subsequent inactivation via neutralization with an acid. The alkali metal alkoxides include the sodium, potassium and lithium alkoxides derived from monohydric alcohols such as methanol, ethanol, propanol, isopropanol, butanol, isobutanol, and pentanol. Especially satisfactory and preferred is sodium methoxide.

In place of or in conjunction with the alkali metal alkoxides, other catalysts which can be utilized are the alkali metal amides, such as sodium amide, potassium amide and lithium amide; and the alkali metal aminoalkoxides containing from 1 to 5 carbon atoms, the latter being derived, by way of example, by the interaction of an alkali metal such as sodium, potassium or lithium with an hydroxy amine such as monoethanol amine, diethanol amine, monoisopropanol amine, or other hydroxy amines, or by dehydration of an alkali metal hydroxide solution in the hydroxy amine.

The amount of catalyst used is an effective catalytic amount which in general ranges upward from about 0.1 mol percent to about 20 mol percent based on the ester fed. Although greater amounts can be used, such is usually unnecessary and creates problems of removal or recovery and expense. Preferably the amount of catalyst is from about 1 to about 10 percent (mol basis). Typically, the amount of catalyst is about 9 percent. The amidation reaction may be carried out without a solvent or with the aid of a solvent such as methanol, which is a particularly powerful solvent for the lower alkyl amines. In some instances, it is convenient to supply alkali metal alkoxide as a solution in alcohol solvent retaining the solvent. In addition, alcohol liberated in the reaction, if not removed, may be retained in the reaction system.

Reaction time is important but not critical. In general, the preferred time for each stage is at least the time necessary to reach the conversion desired for that stage. Longer times are permissible but in general one does not use a longer time than necessary so as to avoid delay in processing and to minimize side reactions. Times of from about 30 seconds to about 5 hours for each of the stages are suitable with a time of from about 2 to about 60 minutes preferred for the first stage and from about 5 to 120 minutes preferred for the second stage. Typical reaction times are 20 minutes and 40 minutes for the first and second stages, respectively.

In a preferred combination of certain of the foregoing preferred aspects of the present invention, diethanol amine is reacted at a temperature of from about 40° C. to about 75° C. with a mixture of methyl esters of aliphatic monocarboxylic acids whose acyl groups contain from about 8 to about 20 carbon atoms, said mixture being characterized in that from about 2 1 to about 20 mol percent of said ester mixture is branched ester in which the acyl groups carry in the α position an alkyl substituent at least two carbon atoms in length, said esters being substantially unreactive with diethanol amine. The amount of diethanol amine employed in this reaction is sufficient to convert at least 10 mol percent of the ester mixture into diethanol amides. The product from the preceding reaction is reacted in a second stage with monoethanol amine at a temperature of from about 75° C. to about 125° C. to convert unreacted ester into monoethanol amide. Both said reactions are carried out in the presence of sodium methoxide catalyst.

In a preferred embodiment of the features of the present invention a process is provided for producing alkanol amides in which a di lower alkanol amine is reacted with a mixture of methyl esters of aliphatic monocarboxylic acids whose acyl groups contain from about 8 to about 20 carbon atoms, said mixture being characterized in that from about 2 to about 20 mol percent of said ester mixture is branched ester in which the acyl groups carry in the $\alpha$ position an alkyl substituent at least two carbon atoms in length, said branched ester being substantially unreactive with said amine. The amount of amine employed is sufficient to convert at least 40 mol percent of the ester mixture into dialkanol amides. The product from the preceding reaction is reacted with a mono lower alkanol amine to convert unreacted ester into mono lower alkanol amide. Both said reactions are carried out in the presence of a sodium alkoxide or potassium alkoxide catalyst. Preferably the di lower alkanol amine used in this embodiment is diethanol amine, the mono lower alkanol amine is mono ethanol amine and the catalyst is sodium methoxide. Preferably the esters used in this embodiment are methyl esters of alkanoic acids whose acyl groups have from about 11 to about 15 carbon atoms, especially where the branched ester includes at least one of: (a) methyl 2-ethyl-nonanoate, methyl 2-ethylundecanoate, and methyl 2-ethyltridecanoate and of (b) the methyl ester of one or more of the following acids: undecanoic acid, 2-methyldecanoic acid, tridecanoic acid, 2-methyldodecanoic acid, pentadecanoic acid, and 2-methyltetradecanoic acid.

The present process produces complex mixtures of alkanol amides containing numerous ramifications. The preferred mixtures produced by processing as described herein contain various numbers of carbon atoms in the acyl groups as well as a wide range of ratios of monoalkanol and dialkanol structures. Many of the mixtures have unique and valuable properties in regard to various aspects such as (1) viscosity of aqueous solutions of the amide, (2) the melting point of the amides themselves, and (3) superior washing properties.

One of the desirable properties of the new compositions that can be controlled readily with the present process is viscosity of aqueous solutions. Liquid detergent concentrates are widely used as in liquid dishwashing detergents and in shampoo. These concentrates preferably are quite viscous. The viscosity control aspect provided by certain new amide compositions produced by the present process makes it desirable in some instances to feed to the first stage of the present process less than the stoichiometric amount of di lower alkanol amine required to react with all of the portion of the feed ester present which is free of $\alpha$ positioned alkyl branches having more than one carbon atom. Thus are obtained mixtures which have various dialkanol amide/monoalkanol amide mol ratios such as 50/50, 55/45, 60/40, 65/35, 70/30, 75/25, 80/20, 85/15, 90/10 and 95/5.

Amide mixtures such as the foregoing are preferably produced by the novel two-stage processing sequence as herein described using feed esters and amines that produce directly the desired product distribution; however, the useful compositions that now have been discovered can be produced by blending in appropriate proportions two or more pure or mixed amides produced by this process or by other processes. For example, esters with $C_8$, $C_{11}$, $C_{12}$, $C_{13}$, $C_{14}$ or $C_{15}$ acyl groups may be processed separately or in sub-combinations and where desired the products blended together or blended with amides from other sources.

Certain amide compositions which are preferred from a cost-effectiveness point of view contain acyl groups having from about 11 to about 15 carbon atoms. Amides whose acyl groups have 13 carbon atoms are preferred because of superior viscosity properties; however, synergistic mixtures are obtained where the amides are mixtures wherein some acyl groups have 11 carbon atoms per group, some acyl groups have 13 carbon atoms and some acyl groups have 15 carbon atoms.

Thus, in general, mixtures of the present amides are preferred wherein $C_{13}$ acyl groups constitute from about 10 to about 90 percent of the total acyl groups present, the balance being $C_{11}$ and $C_{15}$ acyl groups in relative proportions of from about 1:10 to about 10:1.

Amide mixtures are highly preferred which have from about 25 to about 75 percent $C_{13}$ acyl groups with the balance being $C_{11}$ and $C_{15}$ acyl groups in relative proportions of from about 1:3 to about 3:1. Preferably, from about 40 to about 50 percent of the acyl groups of the amides are $C_{13}$ acyl groups.

Preferably, the amides are ethanol amides. Preferred mixtures of di lower alkanol amide and mono lower alkanol amide are characterized in that from about 5 to about 10 mol percent thereof is mono lower alkanol amide whose acyl groups carry in the $\alpha$ position an alkyl substituent at least two carbon atoms in length. Where low melting amides are desired, preferably the amide mixture contains at least about 50 mol percent di lower alkanol amide, more preferably at least about 70 mol percent di lower alkanol amide, especially at least about 90 mol percent of di lower alkanol amide.

The amide compositions of the present invention provide at least comparable if not superior properties in regard to one performance criteria or another in relationship to conventional diethanol amides or monoethanol amides whose acyl groups are obtained from natural sources. In addition, the amides of the present invention have the further advantage that their acyl groups can be produced synthetically at low cost.

Preferred amide mixture readily available at low cost particularly when using the present process and preferred starting materials contains from about 10 to about 65 mol percent of lower alkanol amide whose acyl groups carry a methyl group in the $\alpha$ position; however, in especially preferred compositions, from about 12 to about 25 mol percent of the amide mixture of the present invention is lower alkanol amide whose acyl groups carry a methyl group in the $\alpha$ position.

Another preferred amide mixture according to the present invention contains from about 8 to about 55 mol percent mono lower alkanol amide and from about 92 to about 45 mol percent di lower alkanol amide. From about 2 to about 20 mol percent of the amide mixture is mono lower alkanol amide whose acyl groups carry in the $\alpha$ position an alkyl substituent at least two carbon atoms in length. Preferred amides of this embodiment are ethanol amides.

Another preferred amide mixture according to the present invention is from about 25 to about 35 mol percent monoethanol amide and from about 75 to about 65 mol percent diethanol amide. From about 2 to about 20 mol percent thereof is monoethanol amide whose acyl groups carry in the α position an alkyl substituent at least two carbon atoms in length.

Another preferred amide mixture according to the present invention is about 30 mol percent monoethanol amide and about 70 mol percent diethanol amide. From about 2 to about 20 mol percent thereof is monoethanol amide whose acyl groups carry in the α position an alkyl substituent at least two carbon atoms in length.

Each of the alkanol amide mixtures of the three preceding paragraphs is characterized in that the acyl groups thereof are open chain acyl groups containing from 11 to about 15 carbon atoms. In addition, each of the amide mixtures of the three preceding paragraphs may have one or more of the following especially preferred limitations:

1. The amides thereof contain 11, 13 and 15 carbon atoms in their acyl groups.
2. For each 100 parts by weight thereof there are from about 25 to about 40 parts of amide with $C_{11}$ acyl groups, from about 40 to about 50 parts of amide with $C_{13}$ acyl groups, and from about 20 to about 25 parts of amide with $C_{15}$ acyl groups.
3. From about 10 to about 65 mol percent of the mixture is lower alkanol amide whose acyl groups carry a methyl group in the α position.
4. From about 12 to about 25 mol percent of the mixture is lower alkanol amide whose acyl groups carry a methyl group in the α position.

As noted above, the compositions of this invention can be used with a wide variety of organic detergent surfactants. Included in the category are those classed in the art as anionic detergents, cationic detergents, nonionic detergents, ampholytic (i.e., amphoteric) detergents and zwitterionic detergents, and any suitable mixture of two or more of these (whether from the same class or from different classes). The anionic surface-active compounds are generally described as compounds which contain hydrophilic and lyophilic groups in their molecular structure and which ionize in an aqueous medium to give anions containing the lyophilic group. Typical of these compounds are the alkali metal salts of organic sulfonates or sulfates, such as the alkali metal alkyl aryl sulfonates and the alkali metal salts of sulfates of straight chain primary alcohols. Sodium dodecylbenzene sulfonate and sodium lauryl sulfate are typical examples of these anionic surface-active compounds (anionic synthetic detergents). For a further amplification of anionic organic detergents which can be successfully combined with the amides in accordance with this invention, reference should be had to U.S. Pat. No. 3,422,021, particularly the passage extending from Column 11, line 47 through Column 12, line 15, including the references therein cited, which passage is incorporated herein as if fully set out in this specification.

The cationic detergents are those which ionize in an aqueous medium to give cations containing the lyophilic group. Typical of these compounds are the quaternary ammonium salts which contain an alkyl group of about 12 to about 18 carbon atoms, such as lauryl benzyl dimethyl ammonium chloride. Compounds of this nature are used in detergent formulations for special purposes; e.g., sanitizing and fabric softening.

Nonionic surface-active compounds are generally described as compounds which do not ionize in water solution. Often times these possess hydrophilic characteristics by virtue of the presence therein of an oxygenated chain (e.g., a poly-oxyethylene chain), the lyophilic portion of the molecule being derived from fatty acids, phenols, alcohols, amides or amines. Exemplary materials are the poly-(ethylene oxide) condensates of alkyl phenols (e.g., the condensation product formed from one mole of nonyl phenol and ten moles of ethylene oxide), and the condensation products of aliphatic alcohols and ethylene oxide (e.g., the condensation product formed from 1 mole of tridecanol and 12 moles of ethylene oxide). Reference should be had to U.S. Pat. No. 3,422,021, especially the passage extending from Column 12, line 16 through Column 13, line 26 where a fairly extensive discussion and exemplification of nonionic synthetic detergents is set forth. Inasmuch as the nonionic synthetic detergents set forth in that passage can be successfully used in accordance with this invention, the foregoing passage is incorporated herein as if fully set out in this specification.

The ampholytic surfactants are compounds having both anionic and cationic groups in the same molecule. Exemplary of such materials are derivatives of aliphatic amines which contain a long chain of about 8 to about 18 carbon atoms and an anionic water solubilizing group, e.g., carboxysulfo, sulfo or sulfato. Examples of ampholytic detergents are sodium-3-dodecylaminopropionate, sodium-3-dodecylaminopropane sulfonate, sodium-N-methyl taurate, and related substances such as higher alkyl disubstituted amino acids, betaines, thetines, sulfated long chain olefinic amines, and sulfated imidazoline derivatives.

Zwitterionic synthetic detergents are generally regarded as derivatives of aliphatic quaternary ammonium compounds in which the aliphatic radical may be straight chain or branched and wherein one of the aliphatic substituents contains from about 8 to 18 carbon atoms and one contains an anionic water solubilizing group, e.g., carboxy, sulfo, or sulfato. Examples of compounds falling within this definition are 3-(N,N-dimethyl-N-hexadecyl ammonio)-propane-1-sulfonate and 3-(N,N-dimethyl-N-hexadecyl ammonio)-2-hydroxypropane-1-sulfonate. For a still further appreciation of surface-active compounds (synthetic detergents) which can be employed in the practice of this invention reference may be had, for example, to the disclosures of U.S. Pat. No. 2,961,409 and French Pat. No. 1,398,753.

For a very extensive disclosure of surfactants in general see U.S. Pat. No. 3,526,592 and the various U.S. Patents referred to therein. Inasmuch as the surfactants set forth in these above patents are compatible with the compositions of this disclosure, the foregoing patents are incorporated herein as if fully set out in the specification.

Finished detergent formulations of this invention may contain minor amounts of other commonly used materials in order to enhance the effectiveness or attractiveness of the product. Exemplary of such materials are soluble sodium carboxymethyl cellulose or other soil redeposition inhibitors; perfume; inorganic salts such as sodium chloride, sodium sulfate; alum; fluorescers; dyes or pigments; brightening agents; enzymes; water; alcohols; builder additives, such as the water-soluble salts of ethylenediaminetetraacetic acid, N-(2-hydroxyethyl)- ethylene-diaminetriacetic acid, nitrilotriacetic acid, N-(2-hydroxyethyl)-nitrilodiacetic acid, carboxymethoxy succinic acid, citric acid, and pH adjusters, such as sodium hydroxide, potassium hydroxide, sodium carbonate, sodium bicarbonate and potassium carbonate. In liquid detergent formulations of this invention, the use of hydrotropic agents may be found efficacious. Suitable hydrotropes include the water-soluble alkali metal salts of toluene sulfonic acid, benzene sulfonic acid, and xylene sulfonic acid. Potassium toluene sulfonate and sodium toluene sulfonate are preferred for this use and will normally be employed in concentrations ranging from about 2 to 10 percent by weight based on the total composition.

It will be apparent from the foregoing that the compositions of this invention may be formulated according to any of the various commercially desirable forms. For example, the formulations of this invention may be provided in granular form, in liquid form, in tablet form or in the form of flakes or powders.

The relative proportions and absolute quantities of the several ingredients of the finished compositions of this invention are susceptible to variation and in most cases will vary depending upon such factors as the nature of the particular ingredients being utilized, the end use for which the composition is intended to be put, the relative costs of the ingredients, and the like. For example, the total concentration of the detergent formulations of this invention in water will normally range below about 0.15 percent by weight although it is entirely feasible to utilize higher concentrations where the circumstances warrant or justify the use of higher concentrations. In most cases the aqueous washing solutions of this invention will contain from about 0.05 to about 1 weight percent combined organic detergent surfactant(s) and amide, although concentrates may range up to the limit of solubility. The preferred compositions of this invention are phosphorus-free when desired although it may be desired to include therein normal or reduced quantities of conventional phosphorus-containing materials such as sodium tripolyphosphate, tetrasodium pyrophosphate, salts of substituted methylene diphosphonic containing materials such as sodium tripolyphosphate, tetrasodium pyrophosphate, salts of substituted methylene diphosphonic acids, long chain tertiary phosphine oxides, or the like.

The invention is not to be limited to any particular method of mixing the amide and the detergent. The amide may be mechanically mixed in, crutched in the detergent in the form of a slurry, or dissolved in a solution of the detergent. In addition, the amide system may be admixed with the detergent in any of the forms in which the detergent is manufactured, as well as being added simultaneously or separately to an aqueous solution. In any event, the present amide system is intended to be used with the detergent at the time of application as a cleansing agent.

It is evident that the present process and compositions are disclosed as containing numerous variations and proportions of the materials in regard to: (A) proportions of materials of the three structures: (1) unbranched at the α position, (2) α-methyl branched, (3) α-ethyl, α-propyl and higher alkyl, α positioned branched, as well as of (B) the ratio of ((1) dialkanol amine fed in the first stage to monoalkanol amine fed in the second stage), as well as of (C) numbers of carbon atoms in ((1) acyl groups and (2) the alkanol groups) of mixtures, as well as of (D) organic detergent surfactant and other adjuvants. In the interest of conciseness, the various factors are set forth separately; however, it is intended that the preferred criteria given for the factors operate individually as well as collectively and that therefore cross-reading of the various criteria is contemplated and is hereby specifically disclosed.

The following examples indicate preferred embodiments and aspects of the present invention.

EXAMPLE I

Preparation of $C_{13}$ Amides (9/1 ratio)

To a 200 ml creased flask equipped with a vacuum pump, an agitator, an oil bath for temperature control, and a condensate collector for methanol liberated by the esters, was added 100 grams (0.438 mol) of mixed methyl $C_{13}$ ester containing:

| | Wt. Percent |
|---|---|
| methyl tridecanoate | 80 |
| methyl α-methyl dodecanoate | 14 |
| methyl α-ethyl undecanoate<br>methyl α-propyl decanoate<br>methyl α-butyl nonanoate, etc. | 6 |

The esters were produced by reacting dodecene-1 with CO in the presence of methanol and with cobalt carbonyl catalyst. As is evident, 80 percent of the ester has straight chain $C_{13}$ acyl groups.

To the flask was also added 41.4 grams (0.394 mol) of diethanol amine and 8.4 grams of a 25 wt. percent solution of sodium methoxide catalyst in methyl alcohol. The amount of sodium methoxide was 2.10 grams (0.0388 mol).

The system was evacuated to 32 mm Hg absolute pressure and heated to about 60° C., and held under these conditions for 20 minutes.

Then 2.7 grams (0.044 mol) of monoethanol amine was added and the system was heated to 100° C. and held at that temperature for 39 minutes at 32 mm Hg absolute pressure.

The product weighed 127.5 grams.

After the reaction, the catalyst was neutralized by adding a stoichiometric amount of glacial acetic acid calculated on a basis of the sodium methoxide fed.

A yield of 98.7 percent alkanol amide was obtained.

In this example, the mol ratio of dialkanol amide relative to the monoalkanol amide was about 9/1.

Product impurities were (wt. percent):

| | |
|---|---|
| Ester | |
| methyl tridecanoate | 0.07 |
| methyl α-methyl dodecanoate | 0.19 |
| methyl higher alkyl substituted esters | 0.70 |
| Amine | |
| Diethanol amine | 4.2 |
| Monoethanol amine | 2.7 |

EXAMPLE II

Preparation of $C_{13}$ Amides (9.5/1 Ratio)

Example I was repeated using 100 grams (0.438 mol) of the $C_{13}$ ester, 43.7 grams (0.416 mol) of diethanol amine, 2.70 grams (0.044 mol) of monoethanol amine, and 8.3 grams of the 25 wt. percent solution of sodium methoxide in methyl alcohol. The amount of sodium methoxide was 2.075 grams (0.0384 mol). The mol ratio of catalyst to ester was 0.0877.

The first reaction was for about 17 minutes at about 62°-64° C. and 30 mm of Hg. The second stage reaction time was 40 minutes at 104°-105° C. and 30 mm of Hg.

The product weighed 126.5 grams.

In this example, the mol ratio of dialkanol amide to monoalkanol amide was about 9.5/1.

EXAMPLE III

Preparation of $C_{13}$ Amides (9.5/1 Ratio)

Example II was repeated using 8.4 grams of catalyst solution (0.386 mols $CH_3ONa$, 0.0885 mol ratio of catalyst to ester).

The pressure was atmospheric pressure. Temperature was 56°-105° C. for total time of 35 minutes. The time of addition of the monoethanol amine was not noted; however, the ratio of the reaction times was about the same as in the preceding examples.

The product weighed 129.00 grams.

In this example the mol ratio of dialkanol amide to monoalkanol amide was about 9.5/1.

EXAMPLE IV

Preparation of $C_{13}$ Amides (7/3 ratio)

Example I was repeated using 32.5 grams (0.309 mol of diethanol amine, 11.5 grams (0.109 mol) of monoethanol amine and 8.6 grams of catalyst solution (catalyst content 2.15 grams — 0.0398 mol).

The first stage reaction time was 9 minutes at about 60° C. and at 30 mm of Hg absolute pressure. The second stage reaction time was 46 minutes at about 105° C. and at 30 mm of Hg absolute pressure.

124 Grams of product was obtained which was over 90 percent alkanol amide.

The mol ratio of dialkanol amide to monoalkanol amide was about 7/3.

EXAMPLE V

Preparation of $C_{13}$ Amides (5/5 Ratio)

Example I was repeated using 23 grams (0.219 mol) of diethanol amine, 13.6 grams (0.223 mol) of monoethanol amine and 8.6 grams of catalyst solution (2.15 grams — 0.0398 mol).

The first stage reaction was 13 minutes at about 60° C. and at 30 mm of Hg absolute pressure. The second stage reaction was 44 minutes at about 105° C. and at 30 mm Hg absolute pressure.

116 Grams of product was obtained.

The mol ratio of dialkanol amide to monoalkanol amide was about 5/5.

EXAMPLE IV

Preparation of $C_{11}$ Amides (9/1 Ratio)

Example I was repeated using mixed methyl $C_{11}$ ester containing:

| | Wt. Percent |
|---|---|
| methyl undecanoate | 74.3 |
| methyl α-methyldecanoate | 16 |
| methyl α-ethyl nonanoate | |
| methyl α-propyl octanoate | |
| methyl α-butyl heptanoate, etc. | 9.5 |

This was produced by reacting decene-1 with CO in the presence of methanol and with cobalt carbonyl catalyst.

100 Grams (0.50 mol) of ester, 47.5 grams (0.452 mol) of diethanol amine, 3.10 grams (0.0507 mol) of monoethanol amine and 11.5 grams of 25 percent sodium methoxide solution in methyl alcohol (2.30 grams catalyst - 0.0426 mol) were charged to the flask.

The first stage reaction was for 20 minutes at 60°-65° C. and at about 32 mm Hg absolute pressure. The second stage reaction was for 41 minutes at about 105°-106° C. and at 29 mm Hg absolute pressure.

The mol ratio of dialkanol amide relative to monoalkanol amide was about 9/1. The product weighed 129 grams.

EXAMPLE VII

Preparation of $C_{15}$ Amides (9/1 Ratio)

Example I was repeated using mixed methyl $C_{15}$ ester containing:

| | Wt. Percent |
|---|---|
| methyl pentadecanoate | 74.2 |
| methyl α-methyl tetradecanoate | 17.0 |
| methyl α-ethyl tridecanoate | |
| methyl α-propyl dodecanoate | |
| methyl α-butyl undecanoate, etc. | 8.8 |

100 Grams (0.39 mol) of ester, 36.9 grams (0.351 mol) of diethanol amine, 2.40 grams (0.039 mol) of monoethanol amine and 7.5 grams of 25 percent sodium methoxide solution in methyl alcohol (1.875 grams - 0.0347 mol) were charged to the flask.

The first stage reaction was for 20 minutes at 63°-64° C. and at about 30 mm Hg absolute pressure. The second stage reaction was for 40 minutes at about 105°-107° C. and at 30 mm Hg absolute pressure.

The mol ratio of dialkanol amide relative to monoalkanol amide was about 9/1. The product weighed 123.5 grams.

EXAMPLE VIII

Example VI was repeated with a diethanol amine/-monoethanol amine ratio proportioned to provide a $C_{11}$ amide product with a mol ratio of diethanol amide to monoethanol amide of about 7/3.

EXAMPLE IX

Example VI was repeated with a diethanol amine/-monoethanol amine ratio proportioned to provide a $C_{11}$ amide product with a mol ratio of diethanol amide to monoethanol amide of about 5/5.

EXAMPLE X

Example VII was repeated with a diethanol amine/-monoethanol amine ratio proportioned to provide a $C_{15}$ amide product with a mol ratio of diethanol amide to monoethanol amide of about 7/3.

EXAMPLE XI

Example VII was repeated with a diethanol amine/-monoethanol amine ratio proportioned to provide a $C_{15}$ amide product with a mol ratio of diethanol amide to monoethanol amide of about 5/5.

EXAMPLE XII

The following mixed ester composition was reacted with a diethanol amine in an amine/ester mol ratio of slightly greater than 1/1 and samples taken every fifteen minutes to determine reaction rates for the various esters. Rate data were taken showing that the straight chain or normal ester methyl tridecanoate was more reactive than the (α-methyl) ester which in turn was more reactive than the α-ethyl, α-propyl, etc. esters.

| | Wt. Percent |
|---|---|
| methyl tridecanoate | 75 |
| methyl α-methyl dodecanoate | 21.5 |
| methyl α-ethyl undecanoate | |
| methyl α-propyl decanoate | |
| methyl α-butyl nonanoate, etc. | 3.5 |

EXAMPLE XIII

Another portion of the ester as used in Example XII was distilled to provide an overhead fraction and a bottoms fraction.

The bottoms fraction had the following analysis and was reacted as in Example XII giving similar relative rate data for the various components.

| | Wt. Percent |
|---|---|
| methyl tridecanoate | 96.0 |
| methyl α-methyl dodecanoate | 3.66 |
| methyl α-ethyl undecanoate | |
| methyl α-propyl decanoate | |
| methyl α-butyl nonanoate, etc. | 0.24 |

This composition can provide a synthetic dialkanol amide of high content of dialkanol amide (90–98 percent) when subjected to a second step reaction with merely a small quantity of monoalkanol amide.

This is an excellent product where the cost of distillation is acceptable but usually one prefers to avoid such costs using the undistilled ester.

EXAMPLE XIV

The overhead fraction from Example XIII had the following analysis and was reacted as in Example XII showing similar relative rate data for the various components.

| | Wt. Percent |
|---|---|
| methyl tridecanoate | 22.1 |
| methyl α-methyl dodecanoate | 60.0 |
| methyl α-ethyl undecanoate | |
| methyl α-propyl decanoate | |
| methyl α-butyl nonanoate | 17.8 |

This illustrates ester compositions which produce amides whose acyl groups have a high percentage of α positioned alkyl group substitution including substitution by alkyl groups having two or more carbon atoms per alkyl group. Although these compositions have desirable performance characteristics, unless the bottoms fraction of Example XIII has premium value for other uses, it is usually preferred to use the undistilled compositions which provide their good properties without involving the distillation expense. The overhead composition of this Example would be of little value as a feed for a base catalyzed amidation process to produce amides without the teachings of the present invention.

EXAMPLES XV-XXIV

Amide compositions of Examples I and IV–XI were combined in various proportions as set forth in Table I to provide a wide variety of mixtures in regard to (1) ratio of diethanol amide to monoethanol amide and (2) molecular weight. The compositions were blended with organic detergent surfactants and tested for washing performance in aqueous solutions in several standard ways. The data obtained are set forth in Table II.

Viscosity Test

Viscosity of aqueous solutions containing the mixed amide compositions of subsequent examples was measured using a Haake Roto Visco rotary viscosimeter. Measurements were made at 25° C. and are tabulated herein. Viscosity is expressed as centipoises per second (CPS).

For this test, 15 wt. percent solutions of organic detergent surfactant and amide in water were made. The weight ratio of surfactant to amide was 11/4. The surfactant used was a conventional LAS (linear alkyl benzene sulfonate) (Ultrawet K manufactured by Arco Chemical Co.). Where this LAS is used as a 36.2 weight percent solution, the amount of surfactant used is on dry basis.

This test is used to identify amide compositions that provide a desirably high viscosity of liquid concentrate under standard conditions. In general, the higher viscosity compositions are more desired. The viscosity factor as used herein is the ratio of the viscosity of the test solution relative to the viscosity of a standard amide solution. Thus large values of viscosity factor are desired. The standard amide used was made into a similar 15 percent solution with a 11/4 ratio of surfactant to amide using the same LAS as surfactant and, as amide, a natural source 90 percent lauric-10 percent myristic coconut oil diethanol "super" amide (AA62-X manufactured by Stepan Chemical Co.).

Wetting Time

This is a Draves Wetting Test as described by Harris, J. C., "Detergency Evaluation and Testing", Interscience, 1954, p. 40.

Wetting time is expressed in seconds for a standard hank of string using a standard solution of each amide of a concentration similar to that used by the housewife in washing. Each test solution was an aqueous solution of 0.05 wt. percent total active content wherein the active was sodium lauryl sulfate and amide in a 9/1 weight ratio. Water used was distilled water of 0 ppm hardness. Various alkanol amide compositions including a solution containing AA-62X were tested and results tabulated.

Miniplate Test

This is a standard dishwashing test J. Am. Oil Chem. Soc. 43, 576 (1964) using small plates. Three separate sets of tests were made in water of 0, 50 and 150 ppm of hardness (Ca/Mg mol ratio 3/2). Tests were made at 45° using solutions containing 0.045 wt. percent active. The actives were tested in ternary mixtures containing LAS, AES and amide in 60/30/10 weight ratio. The LAS used was Ultrawet K as used in the viscosity tests. The AES was alcohol ethoxy sulfate (Alfonic 1412-4 of Continental Oil Co.).

Ross-Miles Test

This is a standard foam volume and stability test as described by Harris, J. C., "Detergency Evaluation and Testing", Interscience 1954, p. 47. The test was made at 40° C. using aqueous solutions containing 0.050 wt. percent total active, with foam heights measured in millimeters at the start of the test and also 5 minutes later.

The active solution used was a 9/1 SLS/amide solution in distilled water as used for the wetting time test.

EXAMPLE XV

This composition contained a mixture of dialkanol amide and monoalkanol amide in approximately a 9/1 mol ratio and with $C_{11}$, $C_{13}$ and $C_{15}$ amide weight ratios of 40/40/20 formed by blending product of Examples I, VI and VII. This is an excellent composition with a melting point below 25° C. It is an easily handled liquid at room temperatures. It has the benefit of being a low cost synthetic source material which is at least comparable to and in some respects slightly better than the natural source coconut oil diethanol super amide used as a standard. It is a preferred composition in many ways. Blending data for this and subsequent examples are tabulated in Table I. Performance data for this and subsequent examples are tabulated in Table II.

EXAMPLE XVI

This amide mixture composition had a 9/1 mol ratio of dialkanol amide to monoalkanol amide and $C_{11}$, $C_{13}$ and $C_{15}$ amide weight ratios of 25/50/25 and was formed by blending product from Examples I, VI and VII. Like the product of Example XV, this composition has melting point below 25° C. providing a highly desired product that can be handled as a liquid at room temperature. Performance-wise this composition is superior to the natural source coconut oil derived diethanol super amide in virtually all performance aspects tested. The viscosity was more than 25 percent higher (better) for this amide mixture in comparison to the AA62-X dialkanol super amide. It was superior to the natural source super amide in the wetting test and in the Miniplate washing test. It is a preferred composition in many respects.

EXAMPLE XVII

This amide mixture composition had approximately a 9/1 mol ratio of dialkanol amide to monoalkanol amide and $C_{11}$, $C_{13}$ and $C_{15}$ amide weight ratios of 15/57/28. This composition provided outstanding results in the viscosity test. The viscosity was higher than the standard by a factor of 1.5:1.

EXAMPLE XVIII

This amide mixture composition had approximately a 9/1 mol ratio of dialkanol amide to monoalkanol amide and $C_{11}$, $C_{13}$ and $C_{15}$ amide weight ratios of 10/60/30. This composition provided results similar to those of Example XVII and had an even higher viscosity factor of 1.6:1.

EXAMPLE XIX

This amide mixture composition had approximately a 7/3 mol ratio of dialkanol amide to monoalkanol amide and $C_{11}$, $C_{13}$ and $C_{15}$ amide weight ratios of 40/40/20. As shown in the tabulation, this composition was outstanding in all the performance tests, particularly viscosity, wetting, Miniplate and Ross-Miles and represents a particularly preferred composition.

EXAMPLE XX

This amide mixture composition had approximately a 7/3 mol ratio of dialkanol amide to monoalkanol amide and $C_{11}$, $C_{13}$ and $C_{15}$ amide weight ratios of 25/50/25. This composition was outstanding in the viscosity and Miniplate tests. It is a preferred composition.

EXAMPLE XXI

This amide mixture composition had approximately a 5/5 mol ratio of dialkanol amide to monoalkanol amide and $C_{11}$, $C_{13}$ and $C_{15}$ amide weight ratios of 40/40/20. This composition provided outstanding performance in the Miniplate test and gave high viscosity readings. The comparatively high melting point makes this composition particularly useful in instances where high viscosity is desired and the factor of liquid handling at room temperature is of lesser importance.

EXAMPLE XXII

This amide mixture composition had approximately a 5/5 mol ratio of dialkanol amide to monoalkanol amide and $C_{11}$, $C_{13}$ and $C_{15}$ amide weight ratios of 25/50/25. This composition provided particularly outstanding results in the viscosity and Miniplate tests. Where high viscosity and high miniplate washing factors are desired and the factor of liquid handling at room temperature is less important, this is a particularly valuable and suitable composition.

EXAMPLE XXIII

This amide mixture composition was the 7/3 $C_{13}$ product of Example IV. It is included in the performance data tabulated to show the high viscosity (factor = 2.2) provided by diethanol amide/monoethanol amides having $C_{13}$ acyl groups. Similar viscosity tests of 7/3 $C_{11}$ and 7/3 $C_{15}$ samples provided viscosity factors of about 1.0 but when the $C_{11}$ and $C_{15}$ amides were combined with the $C_{13}$ amide, a synergistic combined viscosity result was obtained as shown by Example XX.

EXAMPLE XXIV

This is a comparative Example using a conventional natural source diethanol lauric-myristic super amide (AA-62X of Stepan Chemical Co.). This product is substantially 100 percent diethanol amide of which 90 percent is lauric ($C_{12}$) and 10 percent is myristic ($C_{14}$). It requires a narrow cut of coconut oil materials rich in the more desirable acyl groups of coconut oil. As is evident, the typical amide compositions of the present invention having synthetic acyl groups are at least equal to this conventional natural source material in most performance aspects which is surprising in itself while each of the present typical compositions is decidedly and unexpectedly superior to the natural source material in at least one of the performance aspects.

TABLE I

| | SYNTHETIC ALKANOL AMIDE MIXTURE COMPOSITIONS | | | | | | | | | | |
|---|---|---|---|---|---|---|---|---|---|---|---|
| | Mol Ratio Dialkanol Amide | Weight Ratio | Blend Parts of Product of Examples | | | | | | | | |
| Example | Monoalkanol Amide | $C_{11}/C_{13}/C_{15}$ | I | IV | V | VI | VII | VIII | IX | X | XI |
| XIV | 9/1 | 40/40/20 | 40 | | | 40 | 20 | | | | |
| XVI | 9/1 | 25/50/25 | 50 | | | 25 | 25 | | | | |
| XVII | 9/1 | 15/57/28 | 57 | | | 15 | 28 | | | | |
| XVIII | 9/1 | 10/60/30 | 60 | | | 10 | 30 | | | | |
| XIX | 7/3 | 40/40/20 | | 40 | | | | 40 | | 20 | |
| XX | 7/3 | 25/50/25 | | 50 | | | | 25 | | 25 | |
| XXI | 5/5 | 40/40/20 | | | 40 | | | | 40 | | 20 |
| XXII | 5/5 | 25/50/25 | | | 50 | | | | 25 | | 25 |
| XXIII | 7/3 | 0/100/0 | | 100 | | | | | | | |

TABLE II

| | PERFORMANCE ASPECTS OF ALKANOL AMIDES | | | | | | | | | | |
|---|---|---|---|---|---|---|---|---|---|---|---|
| | | | | | | | Miniplate Plates Washed at Water Hardness (Avg) | | | Ross-Miles Test 40° C 0.050 wt.% Total Active SAS/Amide = 9/1 | |
| Example | Mol Ratio Di/Mono | Wt. Ratio Amide Mixtures $C_{11}/C_{13}/C_{15}$ | Melting Point ° C | Viscosity CPS | Viscosity Factor | Wetting Time (Seconds) | 0 ppm | 50 ppm | 150 ppm | Initial | 5 Min. |
| XV | 9/1 | 40/40/20 | <25 | 712 | | 41 | 12.3 | 30.0 | 32.0 | 165 | 165 |
| XVI | 9/1 | 25/50/25 | <25 | 890 | 1.26 | 33 | 13.0 | 31.0 | 31.0 | 160 | 155 |
| XVII | 9/1 | 15/57/28 | | 1055 | 1.5 | | 12.0 | 29.0 | 31.0 | | |
| XVIII | 9/1 | 10/60/30 | | 1125 | 1.6 | | 12.3 | 29.0 | 32.0 | | |
| XIX | 7/3 | 40/40/20 | 45 | 1105 | 1.57 | 35 | 15 | 31.0 | 31.0 | 165 | 165 |
| XX | 7/3 | 25/50/25 | 50 | 1245 | 1.77 | 42 | 19.5 | 32.0 | 32.0 | 160 | 160 |
| XXI | 5/5 | 40/40/20 | 57 | 1180 | 1.67 | | 15.6 | | | | |
| XXII | 5/5 | 25/50/25 | 57 | 1410 | 2.0 | | 20.0 | | | | |
| XXIII | 7/3 | 0/100/0 | | 1550 | 2.2 | | | | | | |
| XXIV | 1/0 | 90% $C_{12}$/ 10% $C_{14}$ | 50 | 704 | | 35 | 10.5 | 29.5 | 31.5 | 165 | 160 |

I claim:

1. A process for producing alkanol amide mixtures which comprises:

reacting a di lower alkanol amide with a mixture of lower alkyl esters of aliphatic monocarboxylic acids whose acyl groups contain from about 8 to about 20 carbon atoms, said mixture being characterized in that from about 2 to about 20 mol percent of said ester mixture is branched ester in which the acyl groups carry in the α position an alkyl substituent at least two carbon atoms in length, said branched ester being substantially unreactive with said amine, the amount of said amine employed being sufficient to convert at least 10 mol percent of the ester mixture into di lower alkanol amide; and then reacting the product from the preceding reaction with a mono lower alkanol amine to convert unreacted ester into mono lower alkanol amide, both said reactions being carried out in the presence of a base catalyst.

2. The process of claim 1 wherein the mol ratio of dialkanol amine to lower alkyl esters employed in the first reaction does not exceed about 1.2:1.

3. The process of claim 1 wherein the mol ratio of dialkanol amine to lower alkyl esters employed in the first reaction falls in the range of about 0.4:1 to about 1:1.

4. The process of claim 1 wherein the amount of monoalkanol amine employed in the second reaction is not substantially in excess of the amount required to react with said unreacted ester.

5. The process of claim 1 wherein the mol ratio of monoalkanol amine to said unreacted ester in the second reaction falls in the range of about 0.9:1 to about 1.2:1.

6. The process of claim 1 wherein the mol ratio of dialkanol amine to lower alkyl esters employed in the first reaction falls in the range of about 0.5:1 to about 0.9:1 and the mol ratio of monoalkanol amine to said unreacted ester in the second reaction is in the order of about 1:1.

7. The process of claim 1 wherein from about 5 to about 10 mol precent of said mixture is branched ester in which the acyl groups carry in the α position an alkyl substituent at least two carbon atoms in length.

8. The process of claim 1 wherein said mixture is further characterized in that from about 10 to about 65 mol percent of said mixture is branched ester in which the acyl groups carry a methyl group in the α position.

9. The process of claim 1 wherein said mixture is further characterized in that from about 12 to about 25 mol percent of said mixture is branched ester in which the acyl groups carry a methyl group in the α position.

10. The process of claim 1 wherein the esters are esters of aliphatic monocarboxylic acids whose acyl groups have from about 11 to about 15 carbon atoms.

11. The process of claim 1 wherein the esters are a mixture of esters of aliphatic monocarboxylic acids whose acyl groups have 11, 13 and 15 carbon atoms.

12. The process of claim 1 wherein from about 40 to about 50 percent of the esters reacted have $C_{13}$ acyl groups.

13. The process of claim 1 wherein the temperature of each of said reactions is in the range of about 25° C. to about 150° C.

14. The process of claim 1 wherein the temperature is in the range of about 40° C. to about 75° C. for the first reaction and in the range of about 75° C. to about 125° C. for the second reaction.

15. The process of claim 1 wherein the temperature employed in the second reaction is higher than the temperature employed in the first reaction.

16. The process of claim 1 wherein the catalyst is an alkali metal, an alkali metal alkoxide or an alkali metal amide.

17. The process of claim 1 wherein the catalyst is an alkali metal alkoxide.

18. The process of claim 1 wherein the catalyst is sodium methoxide.

19. The process of claim 1 wherein the lower alkanol amines reacted have from 2 to about 4 carbon atoms per alkanol group.

20. The process of claim 1 wherein the lower alkanol amines reacted are diethanol amine and monoethanol amine, respectively.

21. The process of claim 1 wherein the lower alkanol amines reacted are diisopropanol amine and monoisopropanol amine, respectively.

22. The process of claim 1 wherein the esters reacted are methyl, ethyl, propyl, or butyl esters.

23. The process of claim 1 wherein the esters reacted are methyl esters.

24. The process of claim 1 wherein in the first stage the di lower alkanol amine is added intermittently or continuously to the ester-containing reaction mixture and in the second stage the mono lower alkanol amine is added intermittently or continuously to the amide-containing reaction mixture from the first stage.

25. The process of claim 1 wherein the esters are methyl esters, the di lower alkanol amine is diethanol amine, the catalyst is sodium methoxide, the reaction temperature of the first stage is from about 40° C. to about 75° C., the mono lower alkanol amine is monoethanol amine, and the reaction temperature in the second stage is from about 75° C. to about 125° C.

26. A process for producing alkanol amide mixtures which comprises:

reacting a di lower alkanol amine with a mixture of methyl esters of aliphatic monocarboxylic acids whose acyl groups contain from about 8 to about 20 carbon atoms, said mixture being characterized in that from about 2 to about 20 mol percent of said ester mixture is branched ester in which the acyl groups carry in the $\alpha$ position an alkyl substituent at least two carbon atoms in length, said branched ester being substantially unreactive with said amine, the amount of said amine employed being sufficient to convert at least 40 mol percent of the ester mixture into di lower alkanol amide; and then reacting the product from the preceding step with a mono lower alkanol amine to convert unreacted ester into mono lower alkanol amide, both said reactions being carried out in the presence of a sodium alkoxide or potassium alkoxide catalyst.

27. The process of claim 26 wherein the di lower alkanol amine is diethanol amine, the mono lower alkanol amine is monoethanol amine and the catalyst is sodium methoxide.

28. The process of claim 27 wherein said esters are methyl esters of alkanoic acids whose acyl groups have from about 11 to about 15 carbon atoms.

29. The process of claim 26 wherein said branched ester includes at least one of: methyl 2-ethylnonanoate, methyl 2-ethylundecanoate, and methyl 2-ethyltridecanoate; and wherein said ester mixture includes the methyl ester of one or more of the following acids: undecanoic acid, 2-methyldecanoic acid, tridecanoic acid, 2-methyldodecanoic acid, pentadecanoic acid, and 2-methyltetradecanoic acid.

* * * * *

UNITED STATES PATENT AND TRADEMARK OFFICE
CERTIFICATE OF CORRECTION

PATENT NO. : 4,118,404

DATED : October 3, 1978

INVENTOR(S) : Gunner E. Nelson

It is certified that error appears in the above-identified patent and that said Letters Patent are hereby corrected as shown below:

Cover Page in Item [57], line 5, "groups with a positioned" should read -- groups with $\alpha$ positioned --; Column 1, line 34, "U. S. Pat. Nos. 3,168,553" should read -- U. S. Patent 3,168,553 --; Column 5, line 56, "(n-2/2)" should read -- $\frac{n-2}{2}$ --; Column 10, line 66, "21 to about 20" should read -- 2 to about 20 --; Column 17, line 56, "Example IV" should read -- Example VI --; Column 23, line 6, "XIV" should read -- XV --; Column 23, line 33, "alkanol amide" should read -- alkanol amine --.

Signed and Sealed this

*Eighteenth* Day of *December 1979*

[SEAL]

*Attest:*

SIDNEY A. DIAMOND

*Attesting Officer*

*Commissioner of Patents and Trademarks*